United States Patent
Hasegawa et al.

(10) Patent No.: US 6,709,772 B2
(45) Date of Patent: Mar. 23, 2004

(54) ORGANIC ELECTRICALLY CONDUCTIVE COMPOUND AND AN ORGANIC ELECTROLUMINESCENT DEVICE INCLUDING THE COMPOUND

(75) Inventors: Norio Hasegawa, Atsugi (JP); Akira Shiga, Atsugi (JP); Youichi Itagaki, Atsugi (JP)

(73) Assignee: Mitsumi Electric Co., Ltd., Tokyo (JP)

( * ) Notice: Subject to any disclaimer, the term of this patent is extended or adjusted under 35 U.S.C. 154(b) by 0 days.

(21) Appl. No.: 10/256,894

(22) Filed: Sep. 27, 2002

(65) Prior Publication Data

US 2003/0087128 A1 May 8, 2003

(30) Foreign Application Priority Data

Sep. 27, 2001 (JP) ........................................ 2001-298593
Jun. 6, 2002 (JP) ........................................ 2002-165774

(51) Int. Cl.$^7$ ............................ H05B 33/12; C07F 7/10
(52) U.S. Cl. .................. 428/690; 428/917; 428/448; 313/504; 313/506; 257/40; 548/406; 548/440; 556/410; 556/432
(58) Field of Search ............................... 428/690, 917, 428/447, 448; 313/504, 506; 257/40; 548/406, 416, 427, 440; 556/410, 431, 432; 528/27, 28, 33, 40, 43

(56) References Cited

U.S. PATENT DOCUMENTS 6,310,231 B1 * 10/2001 Igarashi et al. ............. 556/489

* cited by examiner

*Primary Examiner*—Marie Yamnitzky
(74) *Attorney, Agent, or Firm*—Ladas & Parry

(57) ABSTRACT

An organic electrically conductive compound represented by general formula (1):

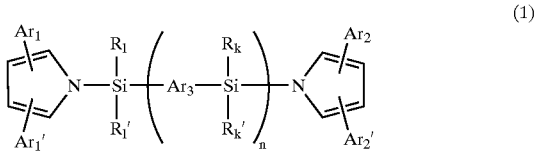

and an organic electroluminescent device using the compound are provided, wherein n is an integer from 1 to 10, k represents any of integers from 2 to n+1, $Ar_1$, $Ar_1'$, $Ar_2$, and $Ar_2'$ are substituted or non-substituted aromatic hydrocarbon rings or heterocyclic rings that share a bond between carbons at 2,3-positions or 4,5-positions of a pyrrole ring in general formula (1) and are fused with the pyrrole ring, respectively, $Ar_3$ is a divalent group of a substituted or non-substituted aromatic hydrocarbon or heterocyclic compound, and $R_1$, $R_1'$, $R_k$, and $R_k'$ are aliphatic hydrocarbon groups or substituted or non-substituted aryl or heterocyclic groups, respectively.

18 Claims, 2 Drawing Sheets

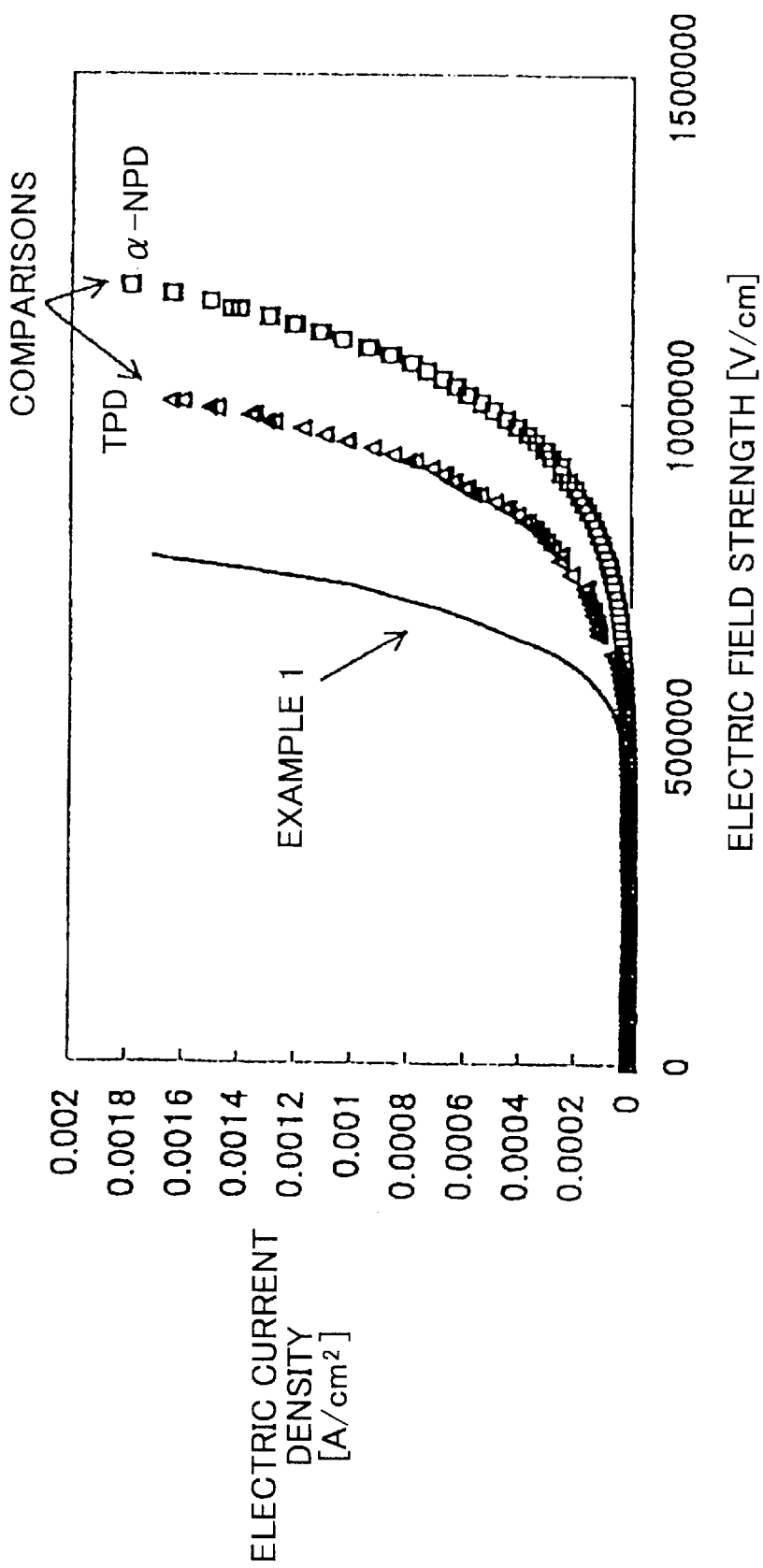

ORGANIC ELECTRICALLY CONDUCTIVE COMPOUND AND AN ORGANIC ELECTROLUMINESCENT DEVICE INCLUDING THE COMPOUND

BACKGROUND OF THE INVENTION

1. Field of the Invention

The present invention generally relates to an organic electrically conductive compound, and an organic electroluminescent device including an organic luminous layer, or an organic luminous layer and one or more organic carrier transportation layers, sandwiched between a cathode and an anode.

2. Description of the Related Art

It is hoped that an organic electroluminescent device is utilized as a display device in various display apparatuses and a light source for illumination such as a backlight, etc., since bright emission can be obtained under application of a low voltage. FIG. 1 shows a typical structure of the organic electroluminescent device, which is a lamination structure of an transparent anode 2, an organic hole transportation layer 3 for efficiently transporting holes injected from the anode 2, an organic luminous layer 4 capable of emitting fluorescence, an organic electron transportation layer 5 for efficiently transporting electrons injected from a metal cathode 6, and the cathode 6, from bottom to top, on a substrate 1. The organic hole transportation layer 3, the organic luminous layer 4, and the organic electron transportation layer 5 are made from respectively suitable organic materials. When DC voltage is applied between both electrodes 2, 6 of such an organic electroluminescent device, electrons are injected from the cathode 6 through the organic electron transportation layer 5 to the organic luminous layer 4 and occupy conduction levels of the layer 4, while holes are injected from the anode 2 through the organic hole transportation layer 3 to the organic luminous layer 4 and occupy valence levels of the layer 4. A fluorescent material constituting the organic luminous layer 4 is excited to a singlet excited state of the material by way of absorption of energy generated by recombination of the electrons moving on the conduction levels and the holes moving on the valence levels in the organic luminous layer 4. As the fluorescent material is energetically relaxed, the material emits fluorescence.

In the organic electroluminescent device with the typical structure as shown in FIG. 1, organic layers such as the organic hole transportation layer 3, the organic luminous layer 4, and the organic electron transportation layer 5 are commonly thin films made from insulating materials. Thus, in order to enable a sufficient electric current to flow through the organic layers under application of voltage to both electrodes 2, 6, it has been needed to improve carrier (hole or electron) injection efficiency controlling an electrical conductivity on the interface between the electrode and the organic layer or between the organic layers, and carrier density and/or carrier mobility in the thin film of the organic layer. Specifically, a metal complex represented by tris(8-hydroxyquinolinato)aluminum (Alq), etc. and arylamines represented by bis[N-(3-methylphenyl)-N-phenyl]benzidine (TPD) and bis[N-(1-naphtyl)-N-phenyl]benzidine (α-NPD) have been employed.

However, since the carrier injection efficiency on an interface between the electrode and the organic layer or between organic layers and the carrier density and carrier mobility in a thin film of the organic layer are low with respect to the organic electroluminescent device employing the above mentioned organic material, the electrical conductivity of the organic electroluminescent device is insufficient and it is required to apply high voltage between the electrodes. There is a problem in that application of the high voltage to both electrodes of the organic electroluminescent device could cause the service life of the device to be shortened.

Also, there is a further problem in that with respect to the organic electroluminescent device employing the above mentioned organic material, the temperature of the device becomes higher due to heat resulting from current carrying and fluorescence emission in the time of driving the device so that peeling on the interface between the cathode and the organic electron transportation layer and oxidation of the cathode could cause the device to deteriorate.

SUMMARY OF THE INVENTION

Accordingly, it is a general object of the present invention to provide an organic compound with a high electrical conductivity and a high heat resistance, in which the above problems are eliminated.

Another object of the present invention is to provide an organic electroluminescent device in which an organic luminous layer or at least one of an organic luminous layer and one or more organic carrier transportation layers contains the organic compound with a high electrical conductivity and a high heat resistance.

To achieve one of the above objects, the present invention provides an electrically conductive compound represented by general formula (1):

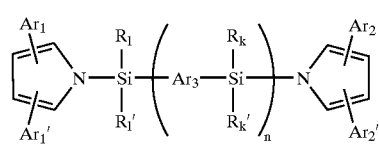

(1)

wherein n is an integer from 1 to 10, k represents any of integers from 2 to n+1, $Ar_1$, $Ar_1'$, $Ar_2$, and $Ar_2'$ are substituted or non-substituted aromatic hydrocarbon rings or heterocyclic rings that share a bond between carbons at 2,3-positions or 4,5-positions of a pyrrole ring in general formula (1) and are fused with the pyrrole ring, respectively, $Ar_3$ is a divalent group of a substituted or non-substituted aromatic hydrocarbon or heterocyclic compound, including 1,4-phenylene group, and $R_1$, $R_1'$, $R_k$, and $R_k'$ are aliphatic hydrocarbon groups or substituted or non-substituted aryl or heterocyclic groups, respectively.

According to the present invention described above, an organic compound with a high electrical conductivity and a high heat resistance can be provided.

The present invention provides the electrically conductive compound described above, wherein at least one of $Ar_1$, $Ar_1'$, $Ar_2$, and $Ar_2'$ is different from the others and/or at least one of $R_1$, $R_1'$, $R_k$, and $R_k'$ is different from the others. That is, all of $Ar_1$, $Ar_1'$, $Ar_2$, and $Ar_2'$ are not identical and/or all of $R_1$, $R_1'$, $R_k$, and $R_k'$ are not identical.

According to the present invention described above, an organic compound with a high electrical conductivity, a high heat resistance and a high transparency can be provided.

The present invention provides an electrically conductive compound represented by formula (2):

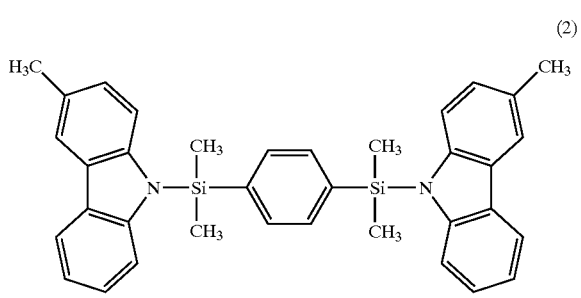

(2)

According to the present invention described above, an organic compound with an excellent electrical conductivity and an excellent heat resistance being easy to synthesize can be provided.

The present invention provides an electrically conductive compound represented by formula (3):

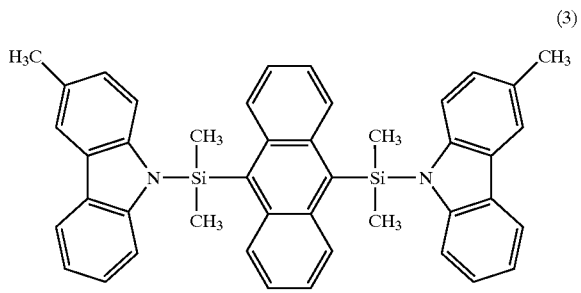

(3)

According to the present invention described above, an organic compound with an excellent electrical conductivity and an excellent heat resistance being easy to synthesize can be provided.

To achieve one of the above objects, the present invention provides an organic electroluminescent device including an organic luminous layer, or an organic luminous layer and one or more organic carrier transportation layers, sandwiched between a cathode and an anode, wherein the organic luminous layer or at least one of the organic luminous layer and the one or more organic carrier transportation layers contains any one of the electrically conductive compounds described above.

According to the present invention described above, an organic electroluminescent device can be provided in which an organic luminous layer or at least one of an organic luminous layer and one or more organic carrier transportation layers contains the electrically conductive compound with a high electrical conductivity and a high heat resistance.

BRIEF DESCRIPTION OF THE DRAWINGS

Other objects, features and advantages of the present invention will become more apparent from the following detailed description when read in conjunction with the accompanying drawings, in which:

FIG. 2 is a graph showing the relationship between electric current density and electric field strength with respect to the measurement device according to the present invention and similar devices for comparison, described in example 1.

DETAILED DESCRIPTION OF THE PREFERRED EMBODIMENTS

Figure 1:
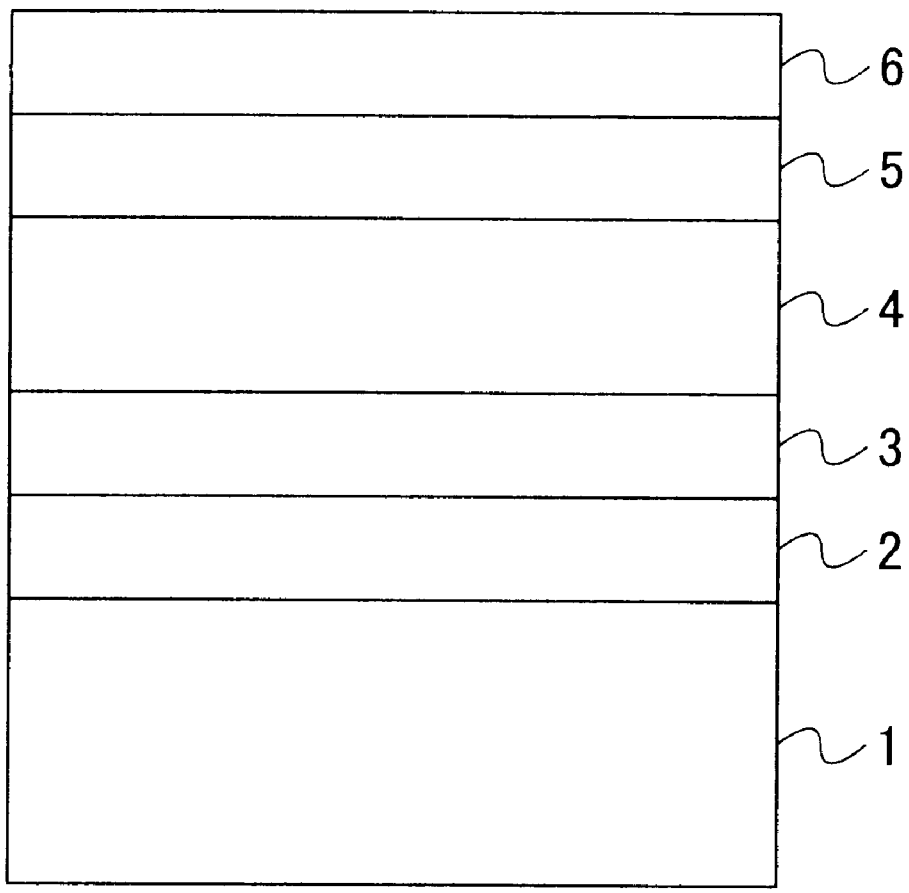
FIG. 1 is a schematic diagram illustrating a basic structure of a typical organic electroluminescent device.

A description of embodiments of the present invention will hereinafter be given by reference to the drawings.

An electrically conductive compound according to the present invention is represented by general formula (1):

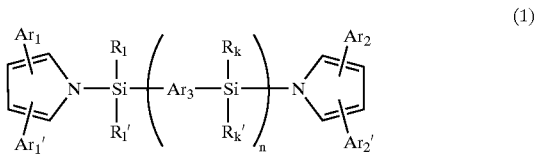

(1)

That is, the electrically conductive compound has one or more structural units including a silicon atom and an aromatic hydrocarbon or heterocyclic ring. Also, two groups including a pyrrole ring structure are bonded to both ends of a main chain composed of the one or more structural units.

Herein, the number n of the structural units including a silicon atom and an aromatic hydrocarbon or heterocyclic ring is an integer of from 1 to 10. If n is an integer equal to or more than 11, it is difficult to synthesize the corresponding compound. Also, it is difficult to form an evaporated film by means of vacuum evaporation since the molecular weight of the compound is too large. Preferably, n is from 1 to 5.

Then, k is the numbering of the one or more structural units including a silicon atom and an aromatic hydrocarbon or heterocyclic ring and represents integers from 2 to n+1 in general formula (1).

$Ar_1$, $Ar_1'$, $Ar_2$, and $Ar_2'$ are substituted or non-substituted aromatic hydrocarbon rings or heterocyclic rings, respectively. The aromatic hydrocarbon ring or heterocyclic ring shares a bond between carbons at 2,3-positions or 4,5-positions of a pyrrole ring in general formula (1) and is fused with the pyrrole ring. For example, if $Ar_1$ is an aromatic hydrocarbon ring or heterocyclic ring sharing a bond between carbons at 2,3-positions of the pyrrole ring, $Ar_1'$ is an aromatic hydrocarbon ring or heterocyclic ring sharing a bond between carbons at 4,5-positions of the same pyrrole ring. $Ar_1$ and $Ar_1'$ may be identical to or different from each other. $Ar_2$ and $Ar_2'$ are similar to $Ar_1$ and $Ar_1'$.

The aromatic hydrocarbon ring allowed to be included in $Ar_1$, $Ar_1'$, $Ar_2$, and $Ar_2'$ is a monocyclic or fused polycyclic aromatic hydrocarbon ring, of which the number of carbon atoms is preferably from 5 to 14. For example, the aromatic hydrocarbon ring is selected from the group consisting of rings of benzene, cyclopentadiene, indene, naphthalene, anthracene, phenanthrene, and biphenyl.

The heterocyclic ring allowed to be included in $Ar_1$, $Ar_1'$, $Ar_2$, and $Ar_2'$ is an aromatic heterocyclic ring, of which the sum of the number of carbon atoms and the number of heteroatoms is preferably from 5 to 14, including at least one of a nitrogen atom, an oxygen atom, and a sulfur atom. For example, the heterocyclic ring is selected from the group consisting of rings of pyrrole, imidazole, pyrazole, pyridine, pyrazine, pyrimidine, furan, thiophene, thiazole, isothiazole, oxazole, isoxazole, quinoline, indole, carbazole, and acridine.

The aromatic hydrocarbon ring and the heterocyclic ring may have a substituent, respectively. The substituent is preferably an alkyl group with from 1 to 10 carbon atoms such as methyl, ethyl, n-propyl, isopropyl, n-butyl, isobutyl, sec-butyl, tert-butyl, n-pentyl, n-hexyl, n-heptyl, n-octyl, n-nonyl, and n-decyl, an alkenyl group with from 2 to 10 carbon atoms such as vinyl, allyl, 1-butenyl, 2-butenyl, and 3-pentenyl, an alkynyl group with from 2 to 10 carbon atoms such as ethynyl, propargyl, and 3-pentynyl, an alkoxy group with from 2 to 10 carbon atoms such as methoxy, ethoxy, propoxy, and butoxy, and a halogen group such as fluoro, chloro, bromo, and iodo.

If all of $Ar_1$, $Ar_1'$, $Ar_2$, and $Ar_2'$ are non-substituted benzene rings, the electrically conductive compound according to the present invention is a compound in which two 9-carbazolyl groups are bonded to both ends of the main chain including a silicon atom and an aromatic hydrocarbon or heterocyclic compound.

$Ar_3$ is a divalent group of substituted or non-substituted aromatic hydrocarbon or heterocyclic compound.

The aromatic hydrocarbon allowed to be included in $Ar_3$ is a monocyclic or fused polycyclic aromatic hydrocarbon, of which the number of carbon atoms is preferably from 5 to 22. For example, the aromatic hydrocarbon is selected from the group consisting of benzene, cyclopentadiene, naphthalene, anthracene, phenanthrene, naphthacene, chrysene, pyrene, pentacene, pentaphene, picene, and perylene.

The heterocyclic compound allowed to be included in $Ar_3$ is an aromatic heterocyclic compound, of which the sum of the number of carbon atoms and the number of heteroatoms is preferably from 5 to 22, including at least one of a nitrogen atom, an oxygen atom, and a sulfur atom. For example, the heterocyclic compound is selected from the group consisting of pyrrole, imidazole, pyrazole, pyridine, pyrazine, pyrimidine, furan, thiophene, thiazole, isothiazole, oxazole, isoxazole, quinoline, indole, carbazole, and acridine.

The aromatic hydrocarbon and the heterocyclic compound may have a substituent, respectively. The substituent is preferably an alkyl group with from 1 to 10 carbon atoms such as methyl, ethyl, n-propyl, isopropyl, n-butyl, isobutyl, sec-butyl, tert-butyl, n-pentyl, n-hexyl, n-heptyl, n-octyl, n-nonyl, and n-decyl, an alkenyl group with from 2 to 10 carbon atoms such as vinyl, allyl, 1-butenyl, 2-butenyl, and 3-pentenyl, an alkynyl group with from 2 to 10 carbon atoms such as ethynyl, propargyl, and 3-pentynyl, an alkoxy group with from 2 to 10 carbon atoms such as methoxy, ethoxy, propoxy, and butoxy, and a halogen group such as fluoro, chloro, bromo, and iodo.

$R_1$, $R_1'$, $R_k$, and $R_k'$ (k=2, . . . , n+1) are aliphatic hydrocarbon groups or substituted or non-substituted aryl or heterocyclic groups, respectively. $R_k$ and $R_k'$ may be identical to or different from each other. $R_1$ and $R_1'$ are similar to $R_k$ and $R_k'$.

The aliphatic hydrocarbon group allowed to be included in $R_1$, $R_1'$, $R_k$, and $R_k'$ may be a straight chain, a branched chain, or cyclic. Preferably, the aliphatic hydrocarbon group is an alkyl group with from 1 to 10 carbon atoms such as methyl, ethyl, n-propyl, isopropyl, n-butyl, isobutyl, sec-butyl, tert-butyl, n-pentyl, n-hexyl, n-heptyl, n-octyl, n-nonyl, and n-decyl, an alkenyl group with from 2 to 10 carbon atoms such as vinyl, allyl, 1-butenyl, 2-butenyl, and 3-pentenyl, an alkynyl group with from 2 to 10 carbon atoms such as ethynyl, propargyl, and 3-pentynyl, a cycloalkyl group with from 3 to 12 carbon atoms such as cyclopropyl, cyclobutyl, cyclopentyl, and cyclohexyl, and alkyl-substituted groups thereof.

The aryl group allowed to be included in $R_1$, $R_1'$, $R_k$, and $R_k'$ is a monocyclic or fused polycyclic aryl group, of which the number of carbon atoms is preferably from 5 to 14. For example, the aryl group is selected from the group consisting of phenyl, 1,3-cyclopentadiene-1-yl, 2-indenyl, 1-naphthyl, 2-naphthyl, 2-anthryl, 2-phenanthryl, and 4-biphenylyl.

The heterocyclic group allowed to be included in $R_1$, $R_1'$, $R_k$, and $R_k'$ is a aromatic heterocyclic group, of which the sum of the number of carbon atoms and the number of heteroatoms is preferably from 5 to 14, including at least one of a nitrogen atom, an oxygen atom, and a sulfur atom. For example, the heterocyclic group is selected from the group consisting of pyrrolyl, imidazolyl, pyrazolyl, pyridyl, pyrazinyl, pyrimidinyl, furyl, thienyl, thiazolyl, isothiazolyl, oxazolyl, isoxazolyl, quinolyl, indolyl, carbazolyl, and acridinyl.

The aryl group and the heterocyclic group may have a substituent, respectively. The substituent is preferably an alkyl group with from 1 to 10 carbon atoms such as methyl, ethyl, n-propyl, isopropyl, n-butyl, isobutyl, sec-butyl, tert-butyl, n-pentyl, n-hexyl, n-heptyl, n-octyl, n-nonyl, and n-decyl, an alkenyl group with from 2 to 10 carbon atoms such as vinyl, allyl, 1-butenyl, 2-butenyl, and 3-pentenyl, an alkynyl group with from 2 to 10 carbon atoms such as ethynyl, propargyl, and 3-pentynyl, an alkoxy group with from 2 to 10 carbon atoms such as methoxy, ethoxy, propoxy, and butoxy, and a halogen group such as fluoro, chloro, bromo, and iodo.

The organic compound according to the present invention is a silicon compound including an aromatic hydrocarbon or heterocyclic ring of a π-electron system and has a higher carrier transportation property or electrical conductivity than that of the above mentioned carrier transportation materials TPD and α-NPD. Also, the organic compound has a higher melting point and thus a higher heat resistance due to the higher molecular weight of the compound. Therefore, the present invention can provide the organic compound with a high electrical conductivity and a high heat resistance.

The organic compound according to the present invention is preferably an asymmetrical molecule. In the present invention, The "asymmetrical" in the molecule means that at least one of $Ar_1$, $Ar_1'$, $Ar_2$, and $Ar_2'$ is different from the others and/or at least one of $R_1$, $R_1'$, $R_k$, and $R_k'$ is different from the others, in the compound represented by formula (1). That is, all of $Ar_1$, $Ar_1'$, $Ar_2$, and $Ar_2'$ are not identical and/or all of $R_1$, $R_1'$, $R_k$, and $R_k'$ are not identical.

In the above case, since the molecule of the electrically conductive compound according to the present invention is asymmetric, the molecules are not regularly arrayed in a solid state of the compound and crystallization of the compound is not facilitated. Thus, the solid of the compound does not become opaque white and keeps a high transparency by suppression of the crystallization in the solid state.

The electrically conductive compound can be synthesized employing, as a starting material, a compound having a main chain including one or more units including a silicon atom and a divalent group of an aromatic hydrocarbon or heterocyclic compound, and two chloro groups bonding to both ends of the main chain. If both ends of the main chain are not bonded to two chloro groups, a compound having hydrogen atoms or methyl groups bonding to both ends of the main chain is treated with a suitable reagent to substitute chloro groups for the hydrogen atoms or methyl groups. Thus, the compound having two chloro groups bonding to both ends of the main chain is prepared as a starting material.

Subsequently, two desired groups that should bond to both ends of a main chain in an objective compound are substituted for the two chloro groups of the starting material, via reaction of the starting material with an organometalic compound with lithium, etc. and the desired group. For example, 9-carbazolyl lithium may be reacted with the starting material to substitute two 9-carbazolyl groups for the two chloro groups bonding to both ends of the main chain. 9-carbazolyl lithium may be synthesized, for example, via reaction of carbazole with n-butyl lithium.

If the compound is not available which has a main chain including one or more units including a silicon atom and a divalent group of an aromatic hydrocarbon or heterocyclic compound and two chloro groups bonding to both ends of the main chain, the compound may be synthesized, for example, via reaction of a chloro-substituted silicon with a dilithio-compound of an aromatic hydrocarbon or heterocyclic compound. The dilithio-compound may be obtained via reaction of a chloro-sunstituted aromatic hydrocarbon or heterocyclic compound with n-butyl lithium.

The examples of the electrically conductive compounds according to the present invention are shown as follows.

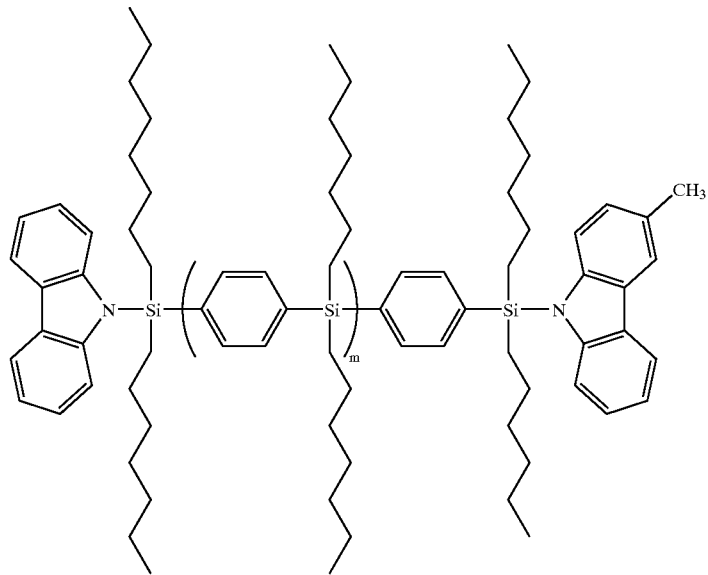

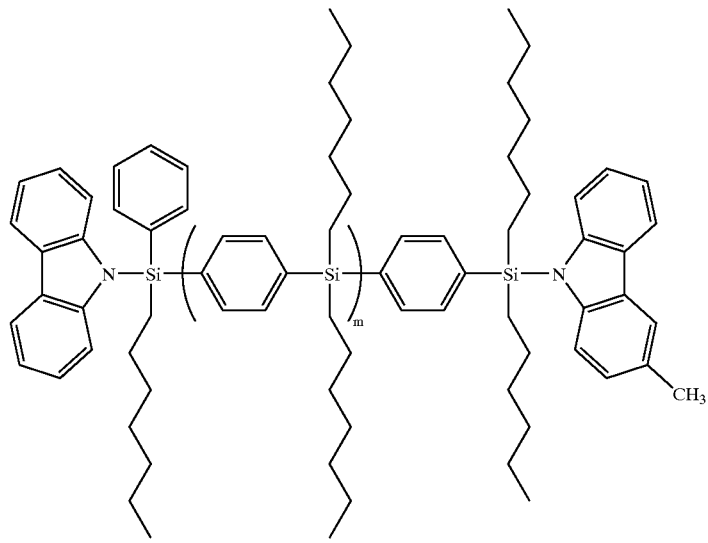

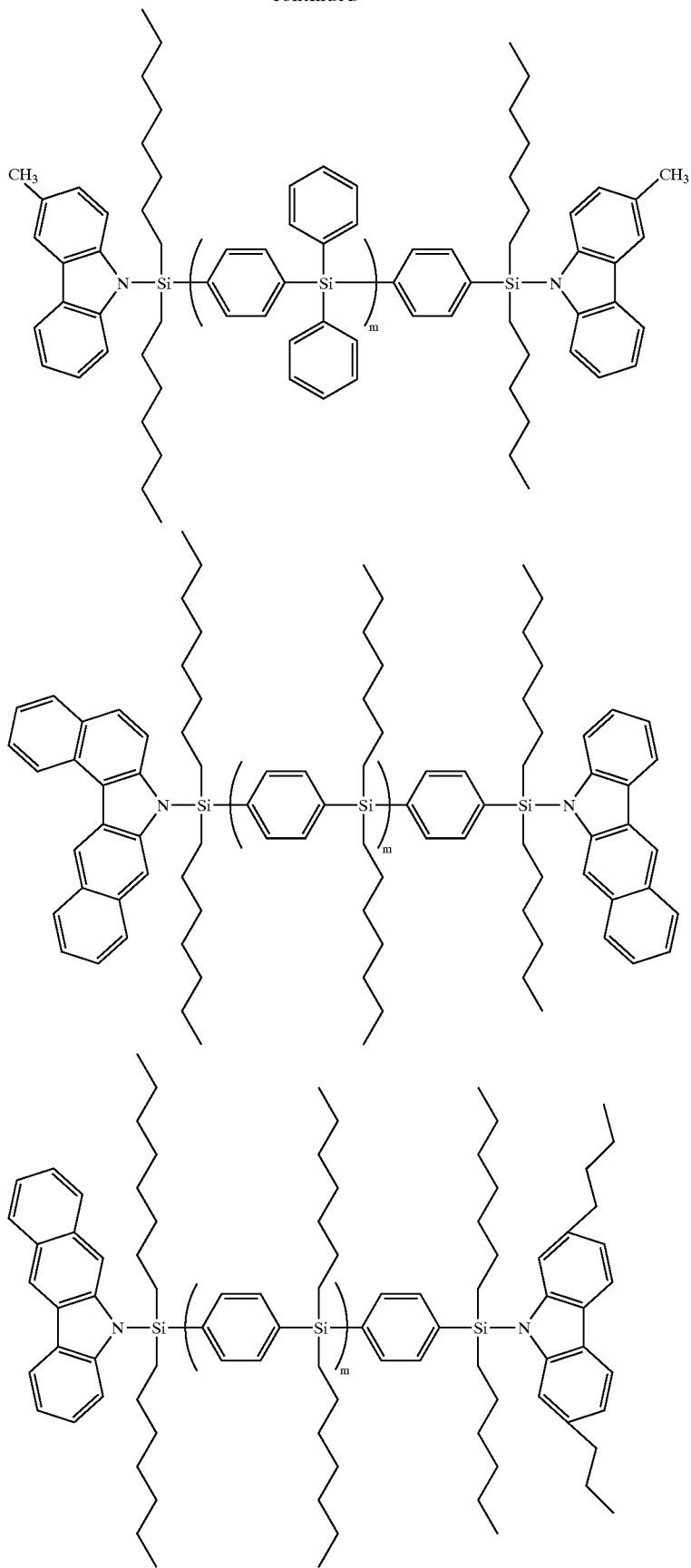

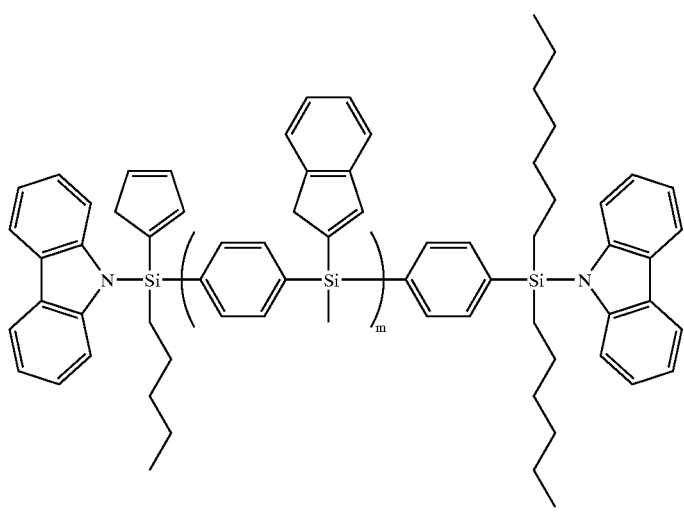
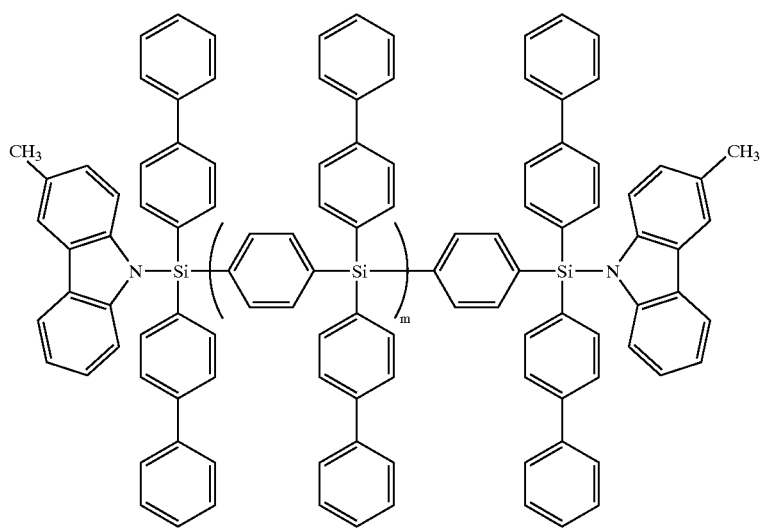
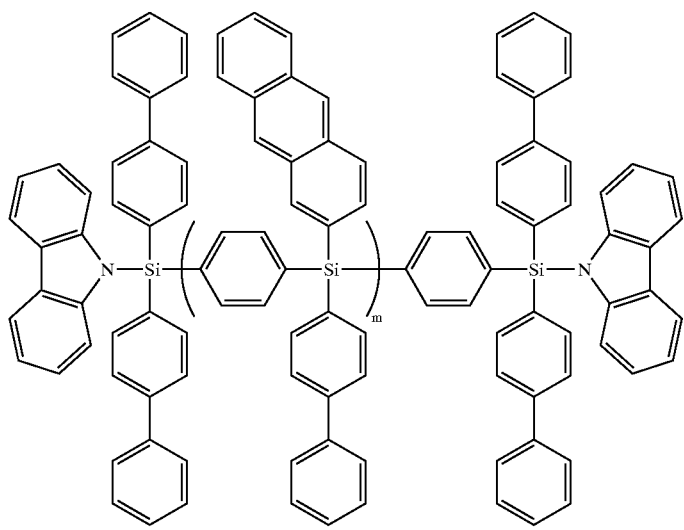

-continued
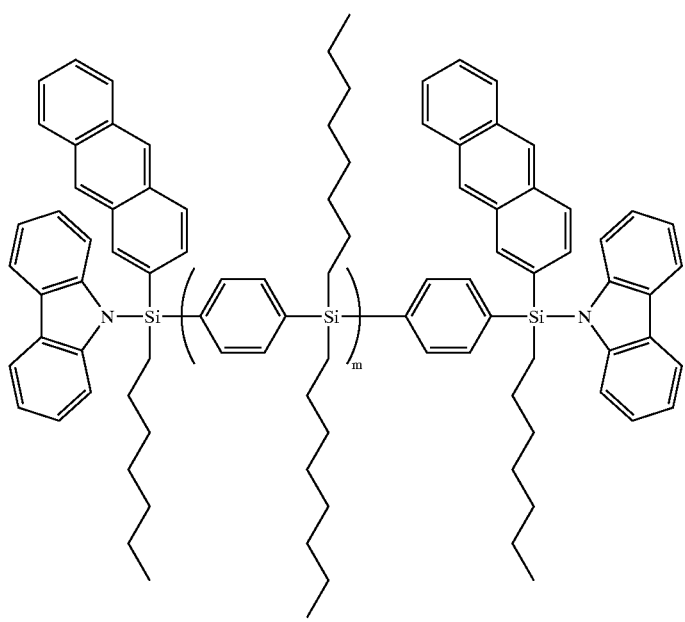
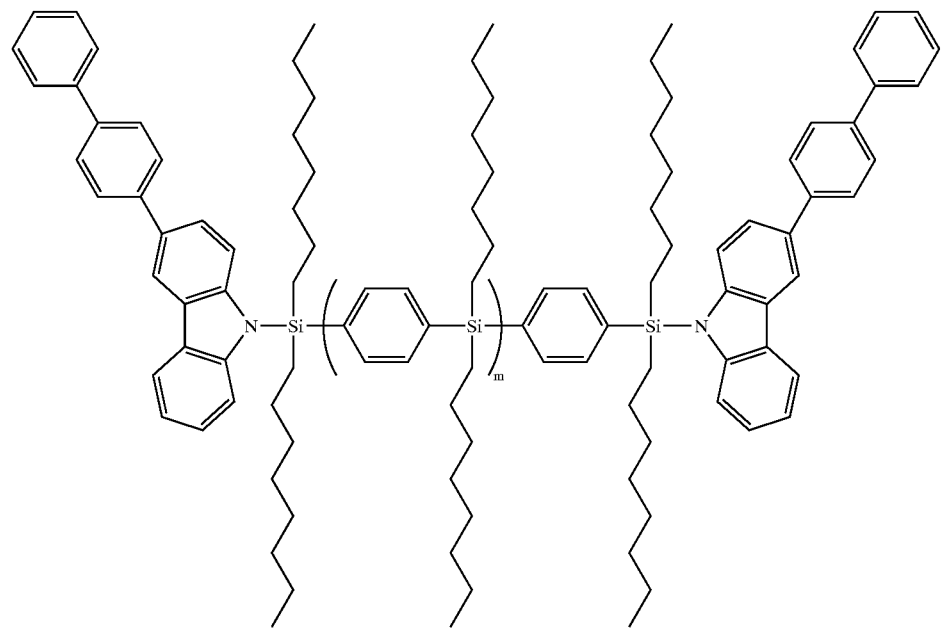

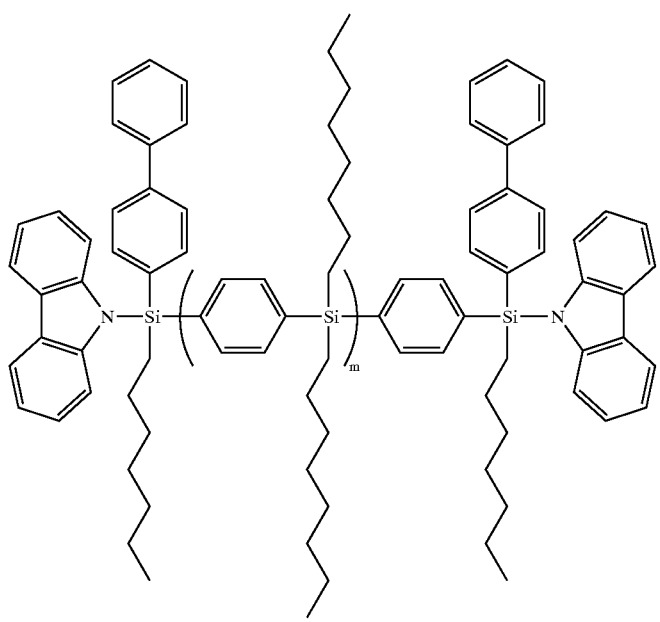
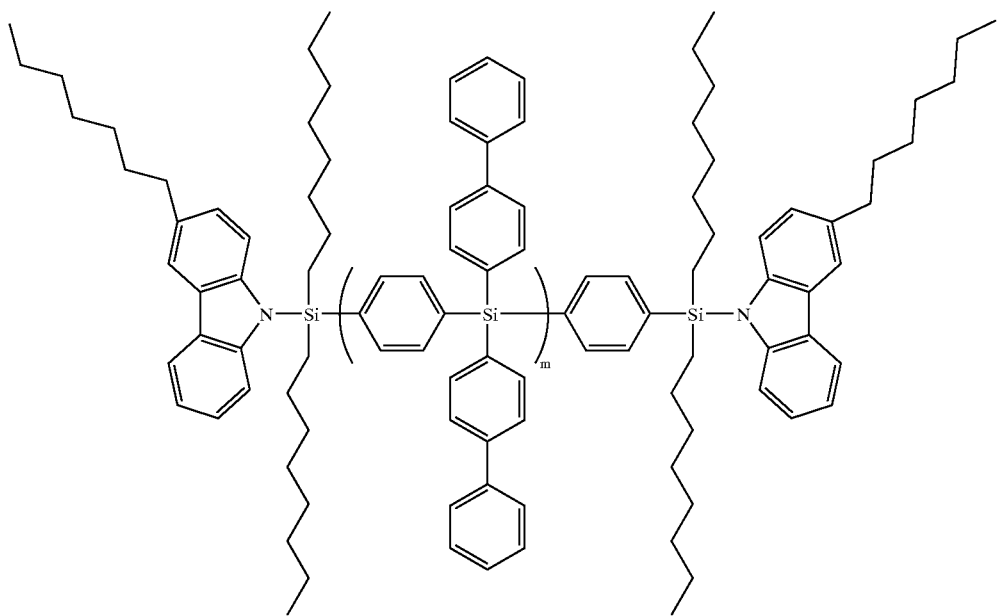

-continued
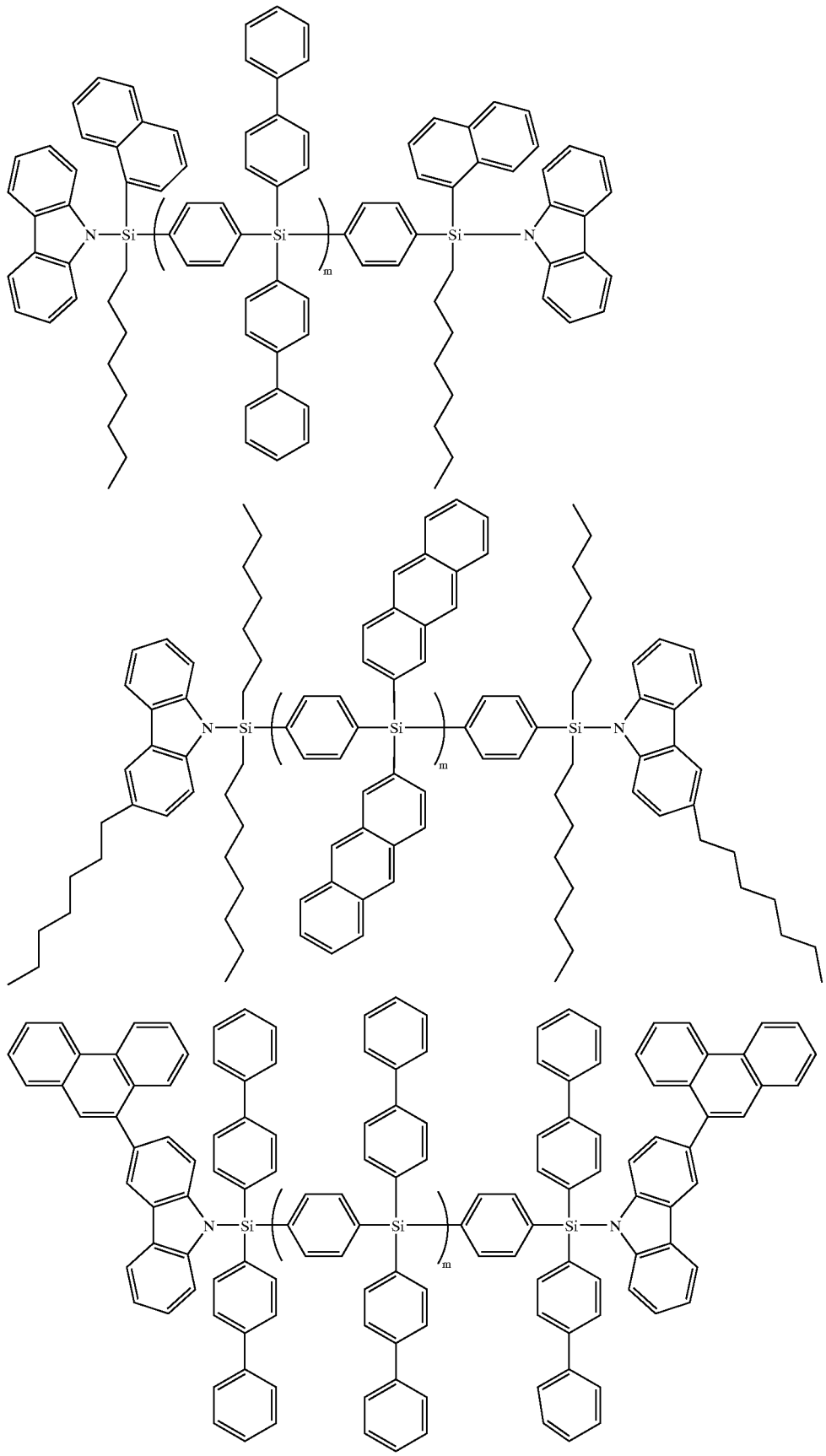

-continued
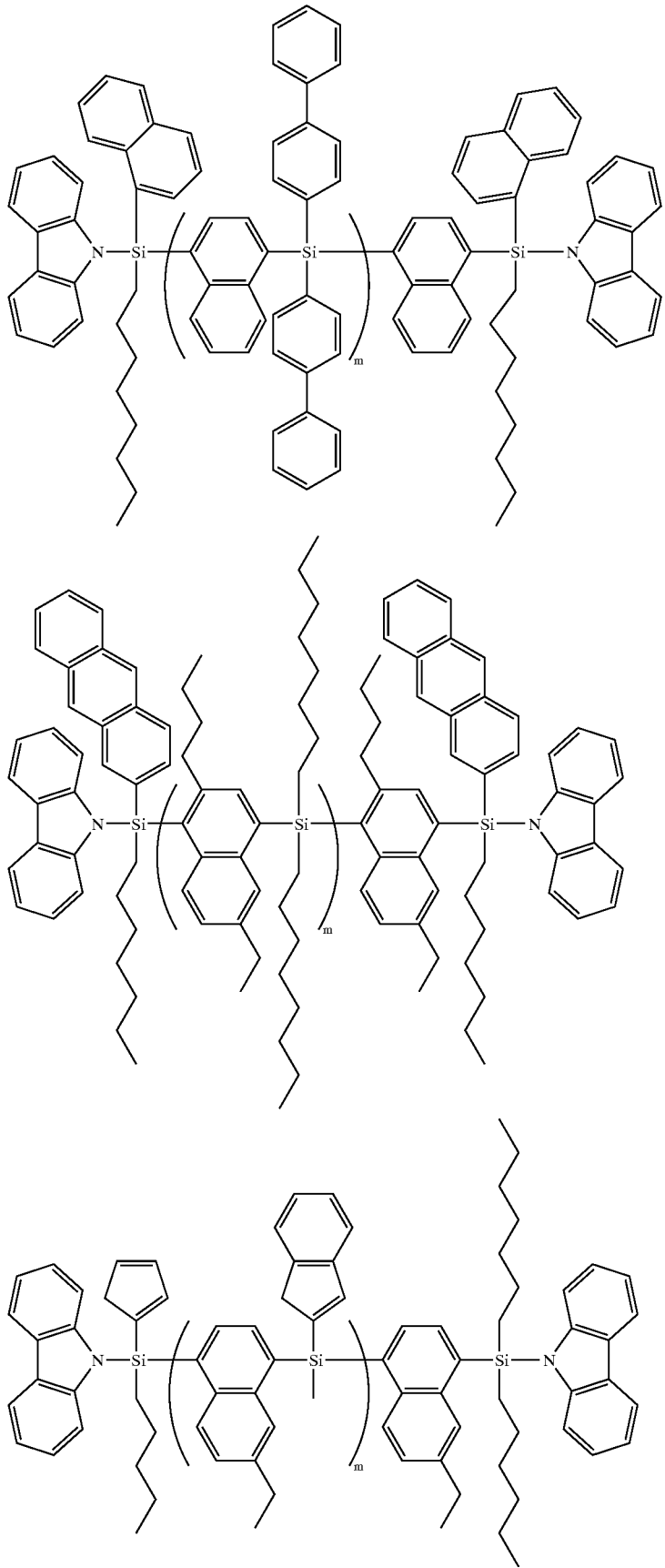

-continued
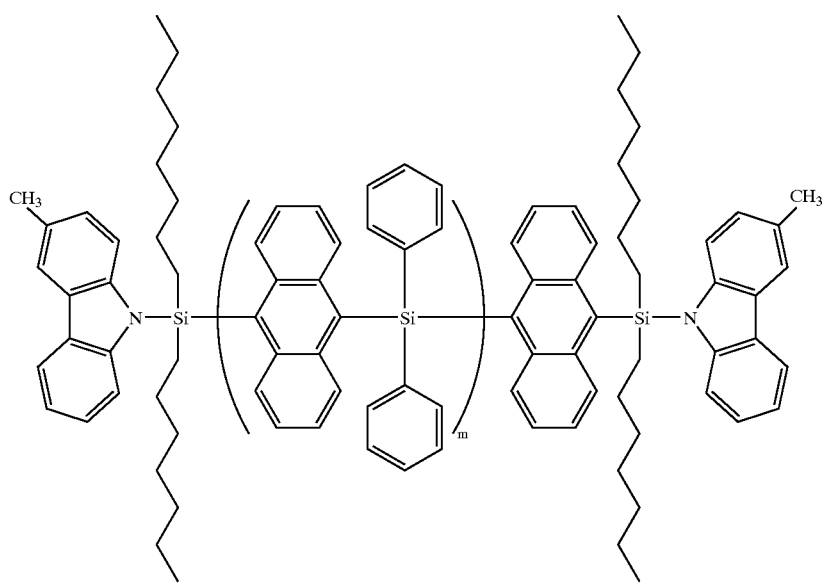
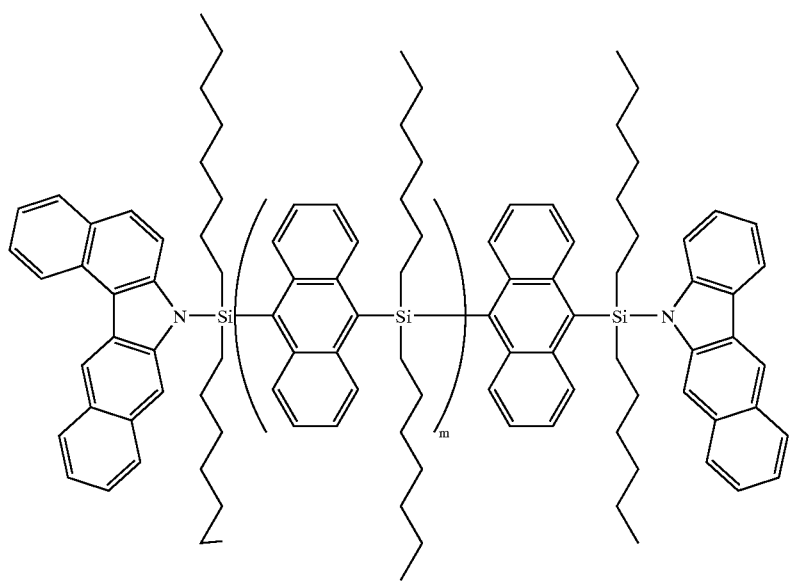

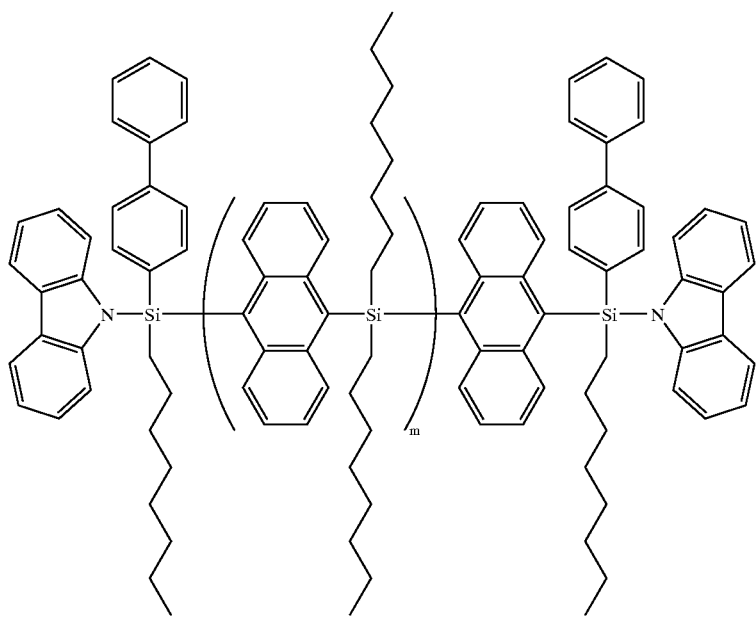
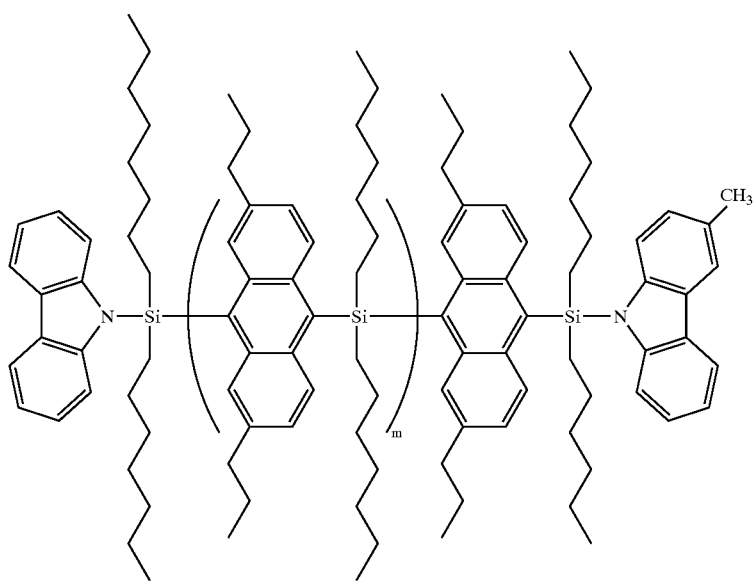

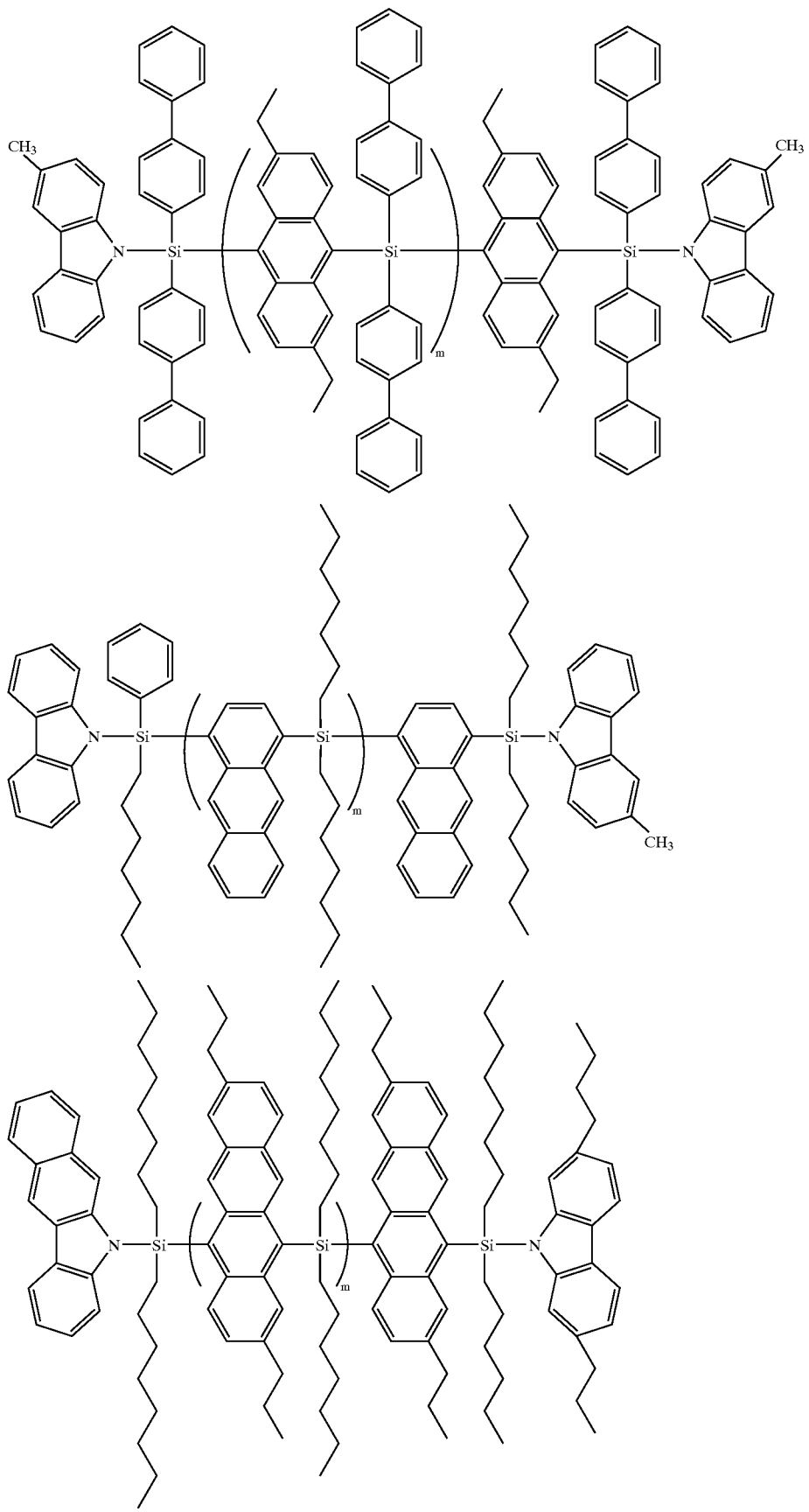

-continued

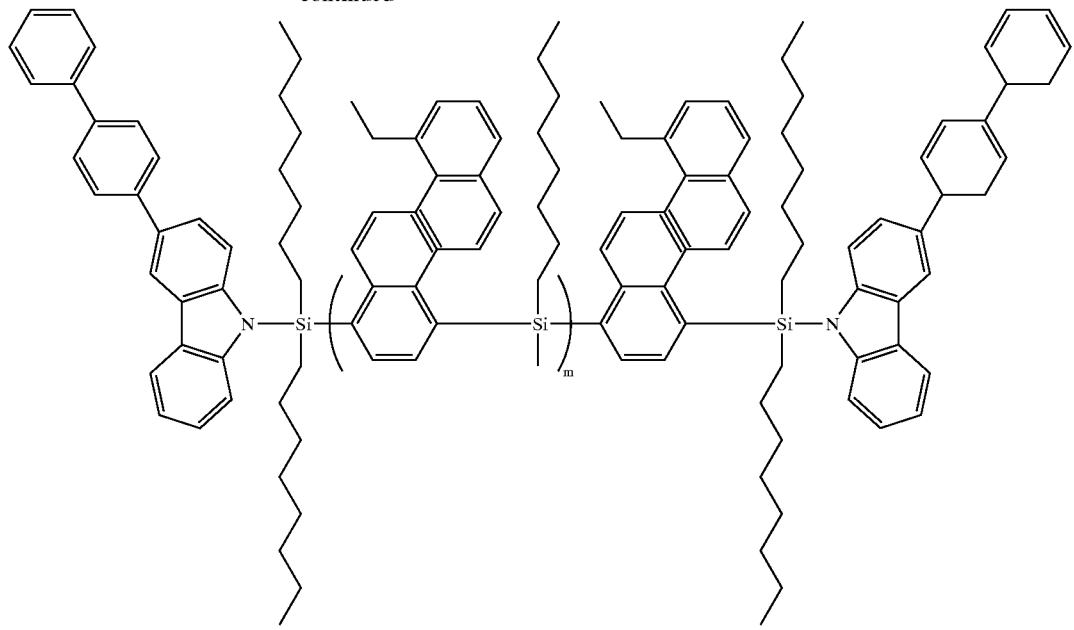

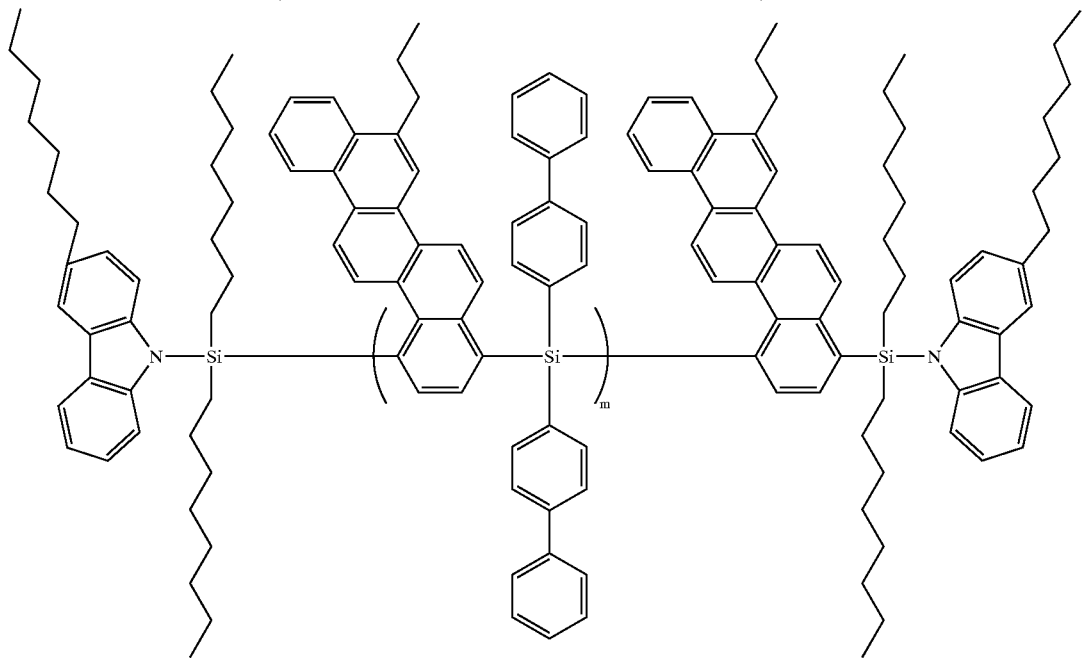

In the chemical formulas, m=n-2, m is an integer equal to or more than 0. Also, a polygonal line represents an alkyl group, a vertex of a polygonal line represents a methylene group, and an end of a polygonal line represents a methyl group. The electrically conductive compound according to the present invention is not limited to the above examples.

The electrically conductive compound according to the present invention is preferably a compound represented by formula (2):

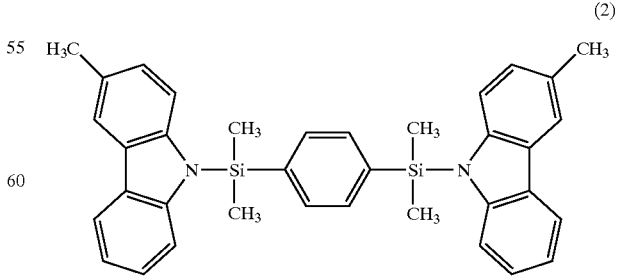

The above compound represented by formula (2) corresponds to a compound represented by general formula (1) in which n is 1, $Ar_1$ and $Ar_2$ are toluene rings of which a bond between carbon atoms at 3,4-positions is identical to a bond between carbon atoms at 2,3-positions of a pyrrole ring, the carbon atom at 3-position of the toluene ring is identical to the carbon atom at 3-position of the pyrrole ring, $Ar_1'$ and $Ar_2'$ are non-substituted benzene rings of which one bond between adjacent carbon atoms is identical to a bond between carbon atoms at 4,5-positions of a pyrrole ring, $Ar_3$ is 1,4-phenylene group, and all of $R_1$, $R_1'$, $R_k$, and $R_k'$ (k=2) are methyl groups. That is, the above compound represented by formula (2) is 1,4-bis[dimethyl(3-methyl-9-carbazolyl) silyl]benzene. The compound has 1,4-phenylene group of an π-electron system between two silicon atoms and two 3-methyl-9-carbazolyl groups of π-electron systems bonding to the silicon atom so that the compound has a high electrical conductivity. Also, since the compound has a large molecular weight of 553, the compound has a high melting point and a high heat resistance. In addition, the compound can be synthesized easily via reaction of 1,4-bis (chlorodimethylsilyl)benzene with an organometalic compound of 3-methylcarbazole and a metal such as lithium, and substitution of two 3-methyl-9-carbazolyl groups for two chloro groups. Moreover, the compound has an advantage in that a thin film made from the compound can be easily formed using a vacuum evaporation machine since n is the smallest integer "1" in general formula (1) and the molecular weight is not too large.

The electrically conductive compound according to the present invention is preferably a compound represented by formula (3):

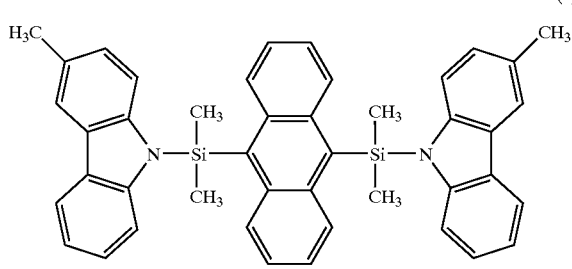

(3)

The above compound represented by formula (3) corresponds to a compound represented by general formula (1) in which n is 1, $Ar_1$ and $Ar_2$ are toluene rings of which a bond between carbon atoms at 3,4-positions is identical to a bond between carbon atoms at 2,3-positions of a pyrrole ring, the carbon atom at 3-position of the toluene ring is identical to the carbon atom at 3-position of the pyrrole ring, $Ar_1'$ and $Ar_2'$ are non-substituted benzene rings of which one bond between adjacent carbon atoms is identical to a bond between carbon atoms at 4,5-positions of a pyrrole ring, $Ar_3$ is 9,10-anthracenediyl group, and all of $R_1$, $R_1'$, $R_k$, and $R_k'$ (k=2) are methyl groups. That is, the above compound represented by formula (3) is 9,10-bis[dimethyl(3-methyl-9-carbazolyl)silyl]anthracene. The compound has 9,10-anthracenediyl group of an π-electron system between two silicon atoms and two 3-methyl-9-carbazolyl groups of π-electron systems bonding to the silicon atom so that the compound has a high electrical conductivity. Also, since the compound has a large molecular weight of 653, the compound has a high melting point and a high heat resistance. In addition, the compound can be synthesized easily via reaction of 9,10-bis(chlorodimethylsilyl)anthracene with an organometalic compound of 3-methylcarbazole and a metal such as lithium, and substitution of two 3-methyl-9-carbazolyl groups for two chloro groups. Moreover, the compound has an advantage in that a thin film made from the compound can be easily formed using a vacuum evaporation machine since n is the smallest integer "1" in general formula (1) and the molecular weight is not too large. Furthermore, the compound represented by formula (3) has a higher electrical conductivity and a higher heat resistance than those of the compound represented by formula (2), since the compound (3) has a more extensive conjugate π-system and larger molecular weight than those of the compound (2).

The electrically conductive compound according to the present invention is suitable not only for a material of an organic layer in an organic electroluminescent device due to the excellent electrical conductivity and the excellent heat resistance but also for use in an electrophotographic photoconductor in a printer and a copy machine, a solar cell, and an image pickup tube, since carrier conductivity of the compound is excellent in the time of photoirradiation to the compound.

Also, the present invention provides an organic electroluminescent device including an organic luminous layer, or an organic luminous layer and one or more organic carrier transportation layers, sandwiched between a cathode and an anode, wherein the organic luminous layer or at least one of the organic luminous layer and the one or more organic carrier transportation layers contains the electrically conductive compound according to the present invention. The organic carrier transportation layer means an organic hole transportation layer or an organic electron transporting layer. Herein, it is preferable that the electrically conductive compound according to the present invention be employed in at least one of the carrier transportation layers.

When the organic hole transporting layer is made from the electrically conductive compound according to the present invention in the typical organic electroluminescent device shown in FIG. 1, the organic electron transporting layer may be made from a material selected from the group consisting of triazole derivatives, oxazole derivatives, oxadiazole derivatives, fluorenone derivatives, carbodiimide derivatives, distyrylpyrazine derivatives, phthalocyanine derivatives, and a metal complex of 8-quinolinol derivatives.

On the other hand, when the organic electron transporting layer is made from the electrically conductive compound according to the present invention in the typical organic electroluminescent device shown in FIG. 1, the organic hole transporting layer may be made from a material selected from the group consisting of carbazole derivatives, triazole derivatives, oxazole derivatives, oxadiazole derivatives, imidazole derivatives, stilbene derivatives, fluorenone derivatives, hydrazone derivatives, and poly(N-vinylcarbazole) derivatives.

In the case of using the electrically conductive compound according to the present invention as a material of the organic luminous layer, since the compound emits singularly weak fluorescence, it is necessary to use the compound in combination with another fluorescent material. The compound according to the present invention may be used in combination with a material selected from the group consisting of styrylbenzene derivatines, oxadiazole derivatives, benzoxazole derivatives, benzothiazole derivatives, benzoimidazole derivatives, cyclopentadiene derivatives, and coumarin derivatines.

The anode is preferably made from a metal or electrically conductive metal oxide with work function of equal to or less than 4 eV to improve hole injection efficiency, such as tin oxide, zinc oxide, indium oxide, indium tin oxide (ITO), gold, silver, chromium, and nickel. Particularly, ITO is desirable as a material of the anode since ITO is transparent, allowing fluorescence emitted from an electroluminescent device to transmit.

The cathode is preferably made from a material selected from the group consisting of alkali metals such as lithium, sodium, and potassium and fluorides thereof, alkali earth metals such as magnesium and calcium and fluorides thereof, aluminum, gold, silver, and lead, taking adhesion property with an adjacent layer, ionization potential, and stability into consideration.

The substrate is commonly made from a glass material and it is desirable to use a no-alkali glass so as to suppress elution of ions from the glass. Otherwise, if necessary, the organic electroluminescent device may be provided with a protective layer to prevent moisture and/or oxygen that deteriorate(s) the device from penetrating into the device. The protective layer is made from any of materials useful for protection from moisture and/or oxygen.

The organic electroluminescent device according to the present invention can be fabricated using the above mentioned materials and a film formation method such as resistance heating deposition method, electron beam method, sputtering method, and coating method appropriately. The film formation method is used for formation of thin films of the organic luminous layer, the hole transporting layer and the electron transporting layer (film thickness of from 1 nm to 5 $\mu$m) and for formation of anode and cathode (film thickness of from 10 nm to 5 $\mu$m).

Thus, a thin film containing the electrically conductive compound according to the present invention is used as an organic layer of an organic electroluminescent device, and an organic electroluminescent device with a high electrical conductivity and a high heat resistance can be provided.

EXAMPLES

Example 1

1,4-bis[dimethyl(3-methyl-9-carbazolyl)silyl]benzene
(Synthesis of the Compound)

The objective compound 1,4-bis[dimethyl(3-methyl-9-carbazolyl)silyl]benzene is synthesized using the steps of:
 reacting 3-methylcarbazole with n-butyl lithium to prepare 3-methyl-9-carbazolyl lithium of an organic lithium compound, and
 reacting the 3-methyl-9-carbazolyl lithium with 1,4-bis(chlorodimethylsilyl)benzene to substitute two 3-methyl-9-carbazolyl groups for two chloro groups.

Specifically, 10 g (0.055 mol) of 3-methylcarbazole was dissolved in 100 ml of dried tetrahydrofuran (THF). 38 ml (1.6 mol/l) of a solution prepared from n-butyl lithium (0.061 mol) and n-hexane was dropped into the THF solution with stirring for 1 hour-at room temperature and the obtained solution was refluxed for 2 hours. After the solution was cooled down to room temperature, 50 ml of a solution prepared from 7.24 g (0.0275 mol) of 1,4-bis(chlorodimethylsilyl)benzene and dried tetrahydrofuran (THF) was dropped for 1 hour and the obtained solution was refluxed for 3 hours. After the solution was cooled down to room temperature, yielded precipitate was removed by means of filtration. The remaining filtrate was concentrated under reduced pressure. After yielded residue was washed with 200 ml of chloroform, 100 ml of water were added. Then, the chloroform phase of the obtained mixture was separated and the remaining aqueous solution was concentrated under reduced pressure. The obtained residue was washed with diethyl ether to obtain 3.2 g of white powder of the objective 1,4-bis[dimethyl(3-methyl-9-carbazolyl)silyl] benzene. The powder of the obtained product had been purified by way of sublimation before the product was used for the following measurements. The purity of the purified product was measured to be 96% by means of gaschromatography.

(Identification of the Compound)

The product synthesized by the above mentioned synthesis method was identified by the following measurements.

The measurement 553 of m/z with respect to the synthesized product was obtained by electro-spray ionization mass spectrometry (ESI-MS), which was consistent to the molecular weight 553 expected from the above formula (2). $^1$H-NMR and $^{13}$C-NMR measurement was performed with respect to a solution of the product in CDCl$_3$. $^1$H-NMR signals at chemical shifts of 0.5–1.5 ppm, 7.0–8.1 ppm, and 7.1–7.8 ppm were obtained, which were identified to absorption signals by $^1$H-atoms of methyl groups, 9-carbazolyl groups, and 1,4-phenylene groups in the compound, respectively. $^{13}$C-NMR signals at chemical shifts of 0–5 ppm and 75–145 ppm were obtained, which were identified to absorption signals by $^{13}$C-atoms of methyl groups, and 9-carbazolyl and 1,4-phenylene groups in the compound, respectively. From the result of the above measurement, the synthesized product was confirmed to be 1,4-bis[dimethyl (3-methyl-9-carbazolyl)silyl]bezene.

(Evaluation for the Compound)

Melting point, emission wavelength, and ionization potential of the product were measured as evaluation for heat resistance, emission property, and electrical conductivity of the product, respectively.

The melting point of the synthesized product was 141° C. and it was confirmed that when the electrically conductive compound according to the present invention is employed in organic layers of an organic electroluminescent device, the organic electroluminescent device with a sufficient heat resistance or stable for heat generation can be provided.

The emission wavelength of the synthesized product was derived from a measurement of photoluminescence (PL). That is, a measurement sample was irradiated with N2-laser (wavelength: 337 nm) as excitation light and emission from the sample was analyzed by a spectrometer to obtain the emission spectrum. The peak wavelength of the emission spectrum was 387 nm and the color of the emission was purple.

The ionization potential of the synthesized product was measured by means of atmospheric ultraviolet photoelectron spectroscopy using a surface analyzer (AC-1M made by Riken Keiki). For the measurement, an evaporated film with the thickness of 100 nm based on the synthesized product was formed onto the glass substrate with the thickness of 0.7 mm using a resistance heating-type vacuum evaporation machine. The ionization potential of the compound according to the present invention obtained from the photoelectron emission spectrum of the evaporated film was 5.8 eV. Thus, since the compound according to the present invention has a comparatively low ionization potential, an electrically conductive material with high carrier injection efficiency can be provided as a material for the organic carrier transportation layer of the organic electroluminescent device.

Furthermore, the relationship between electric current density and electric field strength was measured with respect to the organic electroluminescent device including the compound according to the present invention and compared with the relationship with respect to the similar device including either TPD or α-NPD. For the measurement, a transparent electrically conductive film based on ITO (indium tin oxide) as an anode was formed onto a glass substrate. Then, an evaporated film with the thickness of 100 nm based on the synthesized compound was formed onto the ITO film using a resistance heating-type vacuum evaporation machine. Finally, an aluminum electrode as a cathode was formed onto the evaporated film by means of the same vacuum evaporation method, to fabricate a measurement device. A voltage was applied between the anode and the cathode of the measurement device, and current through the measurement device was measured. The measurement result is shown in FIG. 2 as "EXAMPLE 1", in which the horizontal axis denotes the electric field strength (V/cm) applied to the measurement device and the vertical axis denotes electric current density ($A/cm^2$) or electric current per unit area through the measurement device. The relationships between electric current density and electric filed strength measured with respect to both similar measurement devices including either TPD or α-NPD are also shown in FIG. 2 as "COMPARISONS". Herein, TPD and α-NPD are general organic hole transportation materials. In FIG. 2, when the same electric field strength was applied to the devices, the electric current density of the device including the compound according to the present invention was larger than those of both of the devices including either TPD or α-NPD. That is, it was confirmed that the electrical conductivity of the compound according to the present invention is improved, compared to both TPD and α-NPD. Also, the same electric current density was obtained at lower voltage in the organic electroluminescent device including the compound according to the present invention than in both organic electroluminescent devices including either TPD or α-NPD. Therefore, the present invention can provide an organic electroluminescent device with improved electric current efficiency.

Example 2

9,10-bis[dimethyl(3-methyl-9-carbazolyl)silyl]anthracene (Synthesis of the Compound)

The objective compound 9,10-bis[dimethyl(3-methyl-9-carbazolyl)silyl]anthracene is synthesized using the steps of:

synthesizing 9,10-bis(chlorodimethylsilyl)anthracene synthesized from 9,10-dibromoanthracene, dichlorodimethylsilane, and n-butyl lithium, synthesizing 3-methyl-9-carbazolyl lithium from 3-methylcarbazole and n-butyl lithium, and reacting 9,10-bis(chlorodimethylsilyl)anthracene with 3-methyl-9-carbazolyl lithium to substitute two 3-methyl-9-carbazolyl groups for two chloro groups.

(1) Preparation of 9,10-bis(chlorodimethyl)anthracene

After air within a 1L-volume flask dried in an oven at 120° C. was replaced with argon, 40 g (0.119 mol) of 9,10-dibromoanthracene as a raw material and 400 ml of dried diethyl ether as a solvent were put into the flask. While the obtained solution within the flask was stirred using a stirrer, 98 ml (2.66 mol/l) of a solution of n-butyl lithium (0.261 mol) in n-hexane was dropped into the solution for 1 hour at room temperature using a separating funnel. The solution within the flask was further stirred for 1.5 hours at room temperature to yield a solution of 9,10-dilithioanthracene that is an organic lithium compound.

The obtained solution of 9,10-dilithioanthracene was dropped into a solution prepared from 61.4 g (0.476 mol) of dichlorodimethylsilane and 40 ml of dried diethyl ether as a solvent, in a 1L-volume flask for 2 hours using a separating funnel. After the solution was stirred for 44 hours at room temperature and salt yielded by reaction was removed by means of filtration, the remaining filtrate was concentrated to remove the solvent of the filtrate using an evaporator. The residue was recrystallized in n-pentane to obtain 5.6 g (yield: 13%) of yellow 9,10-bis(chlorodimethylsilyl)anthracene.

(2) Synthesis of 9,10-bis[dimethyl (3-methyl-9-carbazolyl)silyl]anthracene 5 g (0.0276 mol) of 3-methylcarbazole was dissolved in 50 ml of dried tetrahydrofuran and 19 ml (1.6 mol/l) of a solution of n-butyl lithium (0.0304 mol) in n-hexane was dropped into the solution for 1 hour while the solution was stirred at room temperature. After the obtained solution was refluxed for 2 hours and subsequently cooled down to room temperature, 50 ml of a solution prepared from 5 g (0.0138 mol) of 9,10-bis(chlorodimethylsilyl)anthracene in tetrahydrofuran was dropped into the solution for 1 hour. After the obtained solution was refluxed for 3 hours and subsequently cooled down to room temperature, the yielded precipitate was removed by filtration. The filtrate was concentrated under reduced pressure. After the obtained residue was washed with 200 ml of chloroform, 100 ml of water were also added to the residue. The chloroform phase of the obtained mixture was separated by means of solvent extraction and concentrated under reduced pressure. The obtained residue was washed with diethyl ether to obtain 1.5 g (yield: 17%) of yellow powder of objective 9,10-bis[dimethyl(3-methyl-9-carbazolyl)silyl]anthracene. The obtained product was identified by means of IR, $^1$H-NMR, $^{13}$C-NMR, and LC-MS (liquid chromatography—mass spectrometry). In addition, the powder of the product had been purified by way of sublimation before the product was used for the following measurement.

(Evaluation for the Compound)

Melting point, emission wavelength, and ionization potential of the product were measured as evaluation for heat resistance, emission property, and electrical conductivity of the product, respectively.

The melting point of the synthesized product was 237° C. and it was confirmed that when the electrically conductive compound according to the present invention is employed in organic layers of an organic electroluminescent device, the organic electroluminescent device with a sufficient heat resistance or stable for heat generation can be provided.

The emission wavelength of the synthesized product was derived from a measurement of photoluminescence (PL). That is, a measurement sample was irradiated with N2-laser (wavelength: 337 nm) as excitation light and emission from the sample was analyzed by a spectrometer to obtain the emission spectrum. The peak wavelength of the emission spectrum was 459 nm.

The ionization potential of the synthesized product was measured by means of atmospheric ultraviolet photoelectron spectroscopy using a surface analyzer (AC-1M made by Riken Keiki). For the measurement, an evaporated film with the thickness of 100 nm based on the synthesized product was formed onto the glass substrate with the thickness of 0.7 mm using a resistance heating-type vacuum evaporation machine. The ionization potential of the compound according to the present invention obtained from the photoelectron emission spectrum of the evaporated film was 5.55 eV. Thus, since the compound according to the present invention has a comparatively low ionization potential, an electrically conductive material with high carrier injection efficiency can be provided as a material for the organic carrier transportation layer of the organic electroluminescent device.

Furthermore, electron mobility of the compound used in the example 2 was measured by means of the time-of-flight (T.O.F) method. For the measurement, an aluminum electrode with the thickness of 10 nm as an anode was deposited onto a glass substrate. Then, an evaporated film with the thickness of 3.5 μm based on the synthesized compound was formed onto the aluminum electrode. Finally, an aluminum electrode with the thickness of 400 nm as a cathode was deposited onto the evaporated film, to fabricate a measurement device. The anode, the evaporated film, and the cathode were formed using a resistance heating-type vacuum evaporation machine. As a result of the measurement by means of the time-of-flight method, electron mobility of tris(8-hydroxyquinolinato)aluminum (Alq) representative of an electron transportation material was $9.35 \times 10^{-6}$ cm$^2$/Vsec against electric field strength of $7.0 \times 10^5$ V/cm at room temperature (25° C.). On the other hand, electron mobility of the synthesized compound in example 2 was $1.6 \times 10^{-5}$ cm$^2$/Vsec against the same electric field strength of $7.0 \times 10^5$ V/cm and larger than that of Alq. Thus, it is expected that the compound according to the present invention is useful as an electron transportation material.

Further, the present invention is not limited to these embodiments, but various variations and modifications may be made without departing from the scope of the present invention.

The present application is based on Japanese priority applications No.2001-298593 filed on Sep. 27, 2001 and No.2002-165774 filed on Jun. 6, 2002, the entire contents of which are hereby incorporated by reference.

What is claimed is:

1. An electrically conductive compound represented by general formula (1):

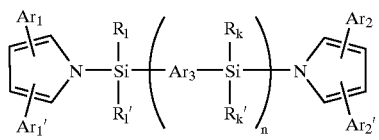

(1)

wherein n is an integer from 1 to 10, k represents any of integers from 2 to n+1, Ar$_1$, Ar$_1$', Ar$_2$, and Ar$_2$' are, independently, substituted or non-substituted aromatic hydrocarbon rings or heterocyclic rings that share a bond between carbons at 2,3-positions or 4,5-positions of a pyrrole ring in the general formula (1) and are fused with the pyrrole ring, Ar$_3$ is a divalent group of a substituted or non-substituted aromatic hydrocarbon or heterocyclic compound, and R$_1$, R$_1$', R$_k$, and R$_k$' are, independently, aliphatic hydrocarbon groups or substituted or non-substituted aryl or heterocyclic groups.

2. The electrically conductive compound as claimed in claim 1, wherein at least one of Ar$_1$, Ar$_1$', Ar$_2$, and Ar$_2$' is different from the others and/or at least one of R$_1$, R$_1$', R$_k$, and R$_k$' is different from the others.

3. The electrically conductive compound as claimed in claim 2, being represented by formula (3):

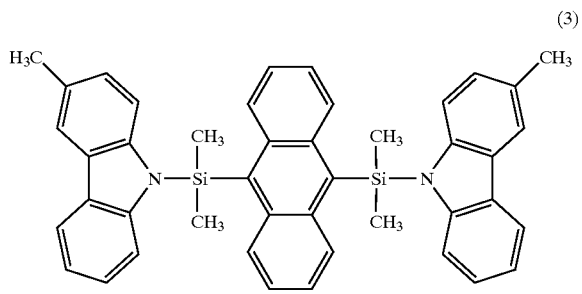

(3)

4. The electrically conductive compound as claimed in claim 1, wherein Ar$_3$ is a 1,4-phenylene group.

5. The electrically conductive compound as claimed in claim 4, wherein at least one of Ar$_1$, Ar$_1$', Ar$_2$, and Ar$_2$' is different from the others and/or at least one of R$_1$, R$_1$', R$_k$, and R$_k$' is different from the others.

6. The electrically conductive compound as claimed in claim 5, being represented by formula (2):

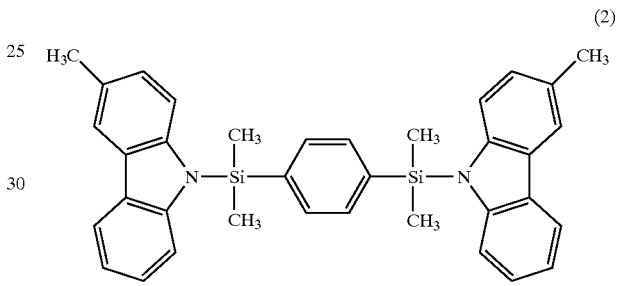

(2)

7. An organic electroluminescent device comprising an organic luminous layer sandwiched between a cathode and an anode, in which the organic luminous layer comprises an electrically conductive compound represented by general formula (1):

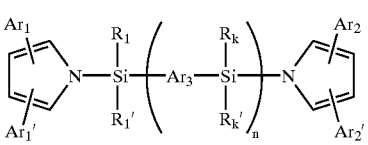

(1)

wherein n is an integer from 1 to 10, k represents any of integers from 2 to n+1, Ar$_1$, Ar$_1$', Ar$_2$, and Ar$_2$' are, independently, substituted or non-substituted aromatic hydrocarbon rings or heterocyclic rings that share a bond between carbons at 2,3-positions or 4,5-positions of a pyrrole ring in the general formula (1) and are fused with the pyrrole ring, Ar$_3$ is a divalent group of a substituted or non-substituted aromatic hydrocarbon or heterocyclic compound, and R$_1$, R$_1$', R$_k$, and R$_k$' are, independently, aliphatic hydrocarbon groups or substituted or non-substituted aryl or heterocyclic groups.

8. The organic electroluminescent device as claimed in claim 7, wherein at least one of Ar$_1$, Ar$_1$', Ar$_2$, and Ar$_2$' is different from the others and/or at least one of R$_1$, R$_1$', R$_k$, and R$_k$' is different from the others.

9. The organic electroluminescent device as claimed in claim 8, wherein the electrically conductive compound is represented by formula (3):

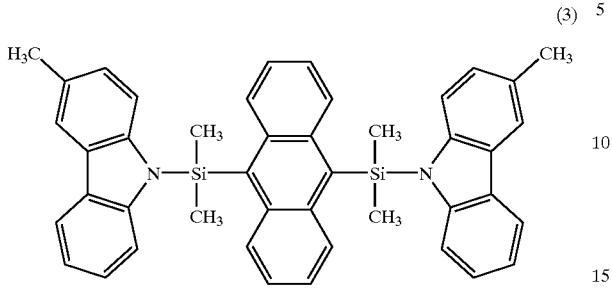

(3)

10. The organic electroluminescent device as claimed in claim 7, wherein $Ar_3$ is a 1,4-phenylene group.

11. The organic electroluminescent device as claimed in claim 10, wherein at least one of $Ar_1$, $Ar_1'$, $Ar_2$, and $Ar_2'$ is different from the others and/or at least one of $R_1$, $R_1'$, $R_k$, and $R_k'$ is different from the others.

12. The organic electroluminescent device as claimed in claim 11, wherein the electrically conductive compound is represented by formula (2):

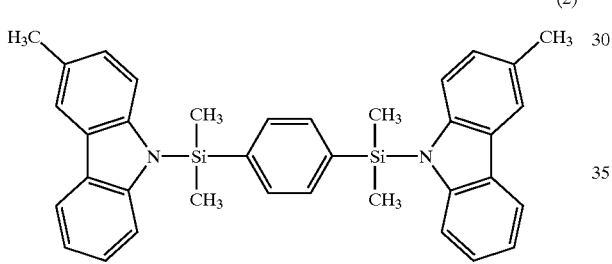

(2)

13. An organic electroluminescent device comprising an organic luminous layer and one or more organic carrier transportation layers, sandwiched between a cathode and an anode, in which at least one of the organic luminous layer and the one or more organic carrier transportation layers comprises an electrically conductive compound represented by general formula (1):

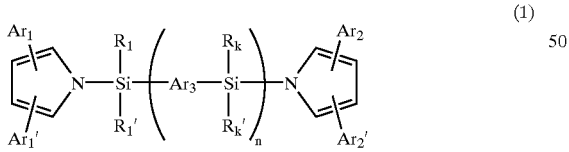

(1)

wherein
n is an integer from 1 to 10,
k represents any of integers from 2 to n+1,
$Ar_1$, $Ar_1'$, $Ar_2$, and $Ar_2'$ are, independently, substituted or non-substituted aromatic hydrocarbon rings or heterocyclic rings that share a bond between carbons at 2,3-positions or 4,5-positions of a pyrrole ring in the general formula (1) and are fused with the pyrrole ring,
$Ar_3$ is a divalent group of a substituted or non-substituted aromatic hydrocarbon or heterocyclic compound, and
$R_1$, $R_1'$, $R_k$, and $R_k'$ are, independently, aliphatic hydrocarbon groups or substituted or non-substituted aryl or heterocyclic groups.

14. The organic electroluminescent device as claimed in claim 13, wherein at least one of $Ar_1$, $Ar_1'$, $Ar_2$, and $Ar_2'$ is different from the others and/or at least one of $R_1$, $R_1'$, $R_k$, and $R_k'$ is different from the others.

15. The organic electroluminescent device as claimed in claim 14, wherein the electrically conductive compound is represented by formula (3):

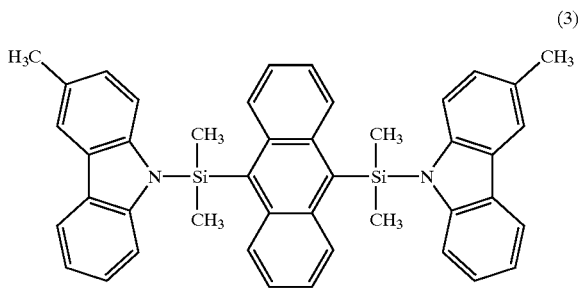

(3)

16. The organic electroluminescent device as claimed in claim 13, wherein $Ar_3$ is a 1,4-phenylene group.

17. The organic electroluminescent device as claimed in claim 16, wherein at least one of $Ar_1$, $Ar_1'$, $Ar_2$, and $Ar_2'$ is different from the others and/or at least one of $R_1$, $R_1'$, $R_k$, and $R_k'$ is different from the others.

18. The organic electroluminescent device as claimed in claim 17, wherein the electrically conductive compound is represented by formula (2):

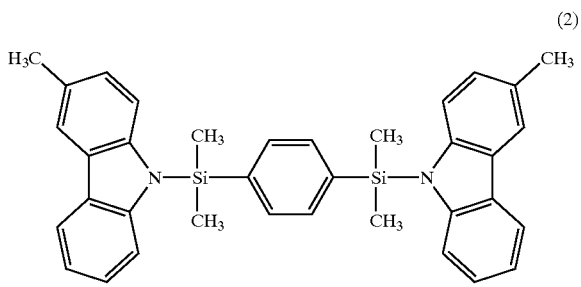

(2)

* * * * *